(12) United States Patent
Koop

(10) Patent No.: US 9,457,182 B2
(45) Date of Patent: *Oct. 4, 2016

(54) LEADLESS CARDIAC PACEMAKER WITH MRI PACING MODE

(71) Applicant: CARDIAC PACEMAKERS, INC., St. Paul, MN (US)

(72) Inventor: Brendan E. Koop, Ham Lake, MN (US)

(73) Assignee: Cardiac Pacemakers, Inc., St. Paul, MN (US)

(*) Notice: Subject to any disclaimer, the term of this patent is extended or adjusted under 35 U.S.C. 154(b) by 0 days.

This patent is subject to a terminal disclaimer.

(21) Appl. No.: 14/834,948

(22) Filed: Aug. 25, 2015

(65) Prior Publication Data

US 2016/0059007 A1 Mar. 3, 2016

Related U.S. Application Data

(60) Provisional application No. 62/042,112, filed on Aug. 26, 2014.

(51) Int. Cl.
| | | |
|---|---|---|
| *A61N 1/00* | (2006.01) | |
| *A61N 1/08* | (2006.01) | |
| *A61N 1/36* | (2006.01) | |
| *A61N 1/365* | (2006.01) | |
| *A61N 1/37* | (2006.01) | |
| *A61N 1/372* | (2006.01) | |
| *A61N 1/375* | (2006.01) | |
| *A61N 1/39* | (2006.01) | |

(52) U.S. Cl.
CPC ............. *A61N 1/08* (2013.01); *A61N 1/36128* (2013.01); *A61N 1/36514* (2013.01); *A61N 1/3718* (2013.01); *A61N 1/3756* (2013.01); *A61N 1/37288* (2013.01); *A61N 1/3931* (2013.01); *A61N 1/3962* (2013.01)

(58) Field of Classification Search
CPC .. A61N 1/08; A61N 1/36128; A61N 1/3718; A61N 1/37288; A61N 1/37217; A61N 1/3962; A61N 1/3956; A61N 1/3756
See application file for complete search history.

(56) References Cited

U.S. PATENT DOCUMENTS

| | | |
|---|---|---|
| 8,019,419 B1 | 9/2011 | Panescu et al. |
| 8,335,563 B2 | 12/2012 | Stessman |
| 8,571,678 B2 | 10/2013 | Wang |
| 8,639,335 B2 | 1/2014 | Peichel et al. |
| 8,744,572 B1 | 6/2014 | Greenhut et al. |
| 2011/0118588 A1 | 5/2011 | Komblau et al. |
| 2011/0160565 A1 | 6/2011 | Stubbs et al. |
| 2011/0160806 A1 | 6/2011 | Lyden et al. |
| 2014/0214104 A1 | 7/2014 | Greenhut et al. |
| 2016/0038746 A1* | 2/2016 | Maile ................ A61N 1/37217 607/4 |

* cited by examiner

*Primary Examiner* — Robert N Wieland
(74) *Attorney, Agent, or Firm* — Seager, Tufte & Wickhem LLP

(57) ABSTRACT

A cardiac rhythm management system includes a first implantable medical device configured to monitor a patient's heart rhythm and provide therapy if appropriate, and a second implantable medical device that is configured to monitor the patient's heart rhythm and provide therapy if appropriate. The first implantable medical device is configured to detect a magnetic field indicative of an MRI machine and, upon detecting a magnetic field indicative of an MRI machine, is further configured to communicate the presence of the magnetic field indicative of the MRI machine to the second implantable medical device. The second implantable medical device may then enter an MRI-safe mode.

20 Claims, 10 Drawing Sheets

LEADLESS CARDIAC PACEMAKER WITH MRI PACING MODE

CROSS REFERENCE TO RELATED APPLICATIONS

This application claims the benefit of U.S. Provisional Patent Application Ser. No. 62/042,112 filed Aug. 26, 2014, the disclosures of each incorporated herein by reference.

TECHNICAL FIELD

The present disclosure generally relates to implantable medical devices and more particularly to implantable cardiac pacemakers.

BACKGROUND

Pacing instruments can be used to treat patients suffering from various heart conditions that may result in a reduced ability of the heart to deliver sufficient amounts of blood to a patient's body. These heart conditions may lead to rapid, irregular, and/or inefficient heart contractions. To help alleviate some of these conditions, various devices (e.g., pacemakers, defibrillators, etc.) can be implanted in a patient's body. Such devices may monitor and provide electrical stimulation to the heart to help the heart operate in a more normal, efficient and/or safe manner. In some cases, a patient may have multiple implanted devices that are configured to communicate information between the devices.

SUMMARY

The present disclosure generally relates to implantable medical devices and more particularly to implantable cardiac pacemakers.

In a first example, a cardiac rhythm management system may include a first implantable medical device configured to monitor a patient's heart rhythm and provide therapy if appropriate, and a second implantable medical device that is configured to monitor the patient's heart rhythm and provide therapy if appropriate. The first implantable medical device is configured to detect a magnetic field indicative of an MRI and, upon detecting a magnetic field indicative of an MRI, is further configured to communicate the presence of the magnetic field indicative of the MRI to the second implantable medical device.

Alternatively, or additionally, and in a second example, the first implantable medical device of the first example is configured to communicate the presence of the magnetic field indicative of an MRI via conducted communication.

Alternatively, or additionally, and in a third example, the second implantable medical device of any of the first through second examples, upon being informed of the presence of the magnetic field indicative of an MRI, is programmed to enter an MRI-safe mode until the first implantable medical device communicates cessation of the magnetic field indicative of an MRI.

Alternatively, or additionally, and in a fourth example, the MRI-safe mode of the third example includes modifying the therapy that would otherwise be provided by the second implantable medical device.

Alternatively, or additionally, and in a fifth example, the MRI-safe mode of the third example includes ceasing the therapy that would otherwise be provided by the second implantable medical device.

Alternatively, or additionally, and in a sixth example, the first implantable medical device of any of the first through fifth examples is configured to communicate the presence of a magnetic field indicative of an MRI upon detecting a static magnetic field having a strength of at least about 0.2 Tesla.

Alternatively, or additionally, and in a seventh example, the first implantable medical device of any of the first through sixth examples includes a beeper and is programmed to operate the beeper to provide the patient with an audible indication that a magnetic field indicative of an MRI has been detected.

Alternatively, or additionally, and in an eighth example, the first implantable medical device of the seventh example is further programmed to operate the beeper to provide the patient with an audible indication that the device has resumed normal operation once the magnetic field is no longer detected.

Alternatively, or additionally, and in a ninth example, in the cardiac rhythm management system of any of the first through eighth examples, the first implantable medical device is an SICD (subcutaneous implantable cardioverter) and the second implantable medical device is a leadless cardiac pacemaker.

Alternatively, or additionally, and in a tenth example, in the cardiac rhythm management system of any of the first through eighth examples, the first implantable medical device is an ICD and the second implantable medical device is one of a neuro-stimulator, a deep brain stimulator and a spinal cord stimulator.

Example eleven is a leadless cardiac pacemaker (LCP) including a housing and two or more electrodes for receiving conducted communication signals emanating from outside of the housing. A receiver is coupled to the one or more electrodes for receiving a communication via conducted communication that indicates the presence of a magnetic field indicative from an MRI. A controller is coupled to the receiver and is configured to cause the leadless cardiac pacemaker to enter an MRI-safe mode upon receiving the communication that indicates the presence of the magnetic field indicative of an MRI.

Alternatively, or additionally, and in a twelfth example, the controller of the eleventh example is configured to remain in the MRI-safe mode until a communication is received that indicates the cessation of the magnetic field indicative from an MRI.

Alternatively, or additionally, and in a thirteenth example, in the leadless cardiac pacemaker of any of the eleventh through twelfth examples, in an operational mode, the controller is configured to monitor a patient's heart rhythm and/or provide a patient therapy; and in the MRI-safe mode, the controller is configured to modify the monitoring of the patient's heart rhythm and/or modify the patient therapy relative to the operational mode.

Alternatively, or additionally, and in a fourteenth example, in the leadless cardiac pacemaker (LCP) of any of the eleventh through twelfth examples, in an operational mode, the controller is configured to monitor a patient's heart rhythm and/or provide a patient therapy; and in the MRI-safe mode, the controller is configured to cease the monitoring of the patient's heart rhythm and/or cease the patient therapy.

Alternatively, or additionally, and in a fifteenth example, in the leadless cardiac pacemaker (LCP) of any of the eleventh through twelfth examples, in an operational mode, the controller is configured to pace and/or sense a heart; and in the MRI-safe mode, the controller is configured to modify the pacing and/or sensing of the heart relative to the operational mode.

Alternatively, or additionally, and in a sixteenth example, in the leadless cardiac pacemaker (LCP) of any of the eleventh through twelfth examples, in an operational mode, the controller is configured to pace and/or sense a heart; and in the MRI-safe mode, the controller is configured to cease the pacing and/or sensing.

Alternatively, or additionally, and in a seventeenth example, the one or more electrodes of any of the eleventh through sixteenth examples form part of an outer surface of the leadless cardiac pacemaker (LCP).

Example eighteen is a method of operating a cardiac rhythm management system including an implantable defibrillator and an implantable leadless pacemaker. A presence of a magnetic field indicative of an MRI is detected via one of the implantable defibrillator or the implantable leadless pacemaker. An indication of the detected magnetic field is communicated to the other of the implantable defibrillator or the implantable leadless pacemaker. A function of the implantable defibrillator or the implantable leadless pacemaker is altered in response to receipt of the communicated indication.

Alternatively, or additionally, and in a nineteenth example, the method of the eighteenth example further includes returning to normal function of the implantable defibrillator or the implantable leadless pacemaker once either the implantable defibrillator or the implantable leadless pacemaker communicates an absence of the detected magnetic field.

Alternatively, or additionally, and in a twentieth example, the implantable defibrillator of any of the eighteenth through nineteenth example detects the magnetic field and communicates the indication of the detected magnetic field to the implantable leadless pacemaker, and in response the implantable leadless pacemaker performs a predefined pacing therapy.

The above summary is not intended to describe each embodiment or every implementation of the present disclosure. Advantages and attainments, together with a more complete understanding of the disclosure, will become apparent and appreciated by referring to the following description and claims taken in conjunction with the accompanying drawings.

BRIEF DESCRIPTION OF THE DRAWINGS

The disclosure may be more completely understood in consideration of the following description of various illustrative embodiments in connection with the accompanying drawings, in which.

Figure 1:
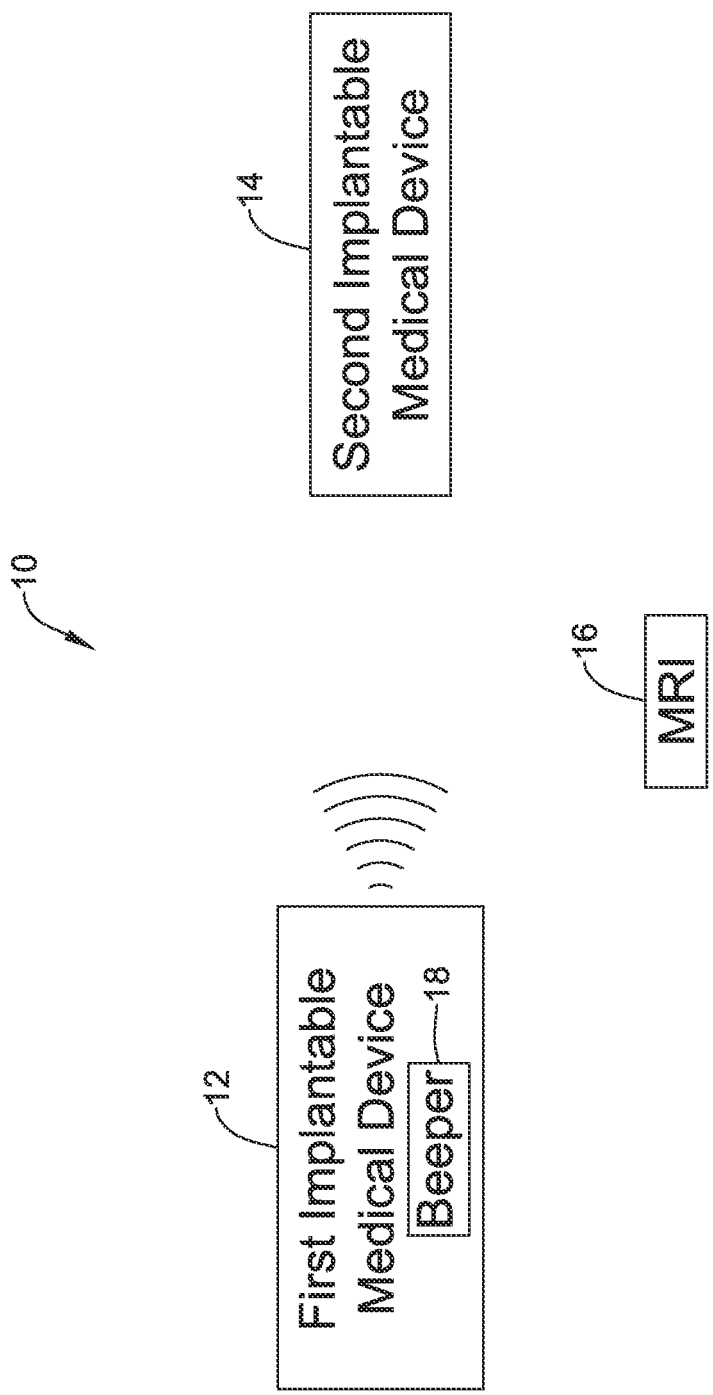
FIG. 1 is a schematic diagram illustrating a cardiac rhythm management system in combination with an MRI machine according to an example of the present disclosure.

While the disclosure is amenable to various modifications and alternative forms, specifics thereof have been shown by way of example in the drawings and will be described in detail. It should be understood, however, that the intention is not to limit aspects of the disclosure to the particular illustrative embodiments described. On the contrary, the intention is to cover all modifications, equivalents, and alternatives falling within the spirit and scope of the disclosure.

DESCRIPTION

The following description should be read with reference to the drawings in which similar elements in different drawings are numbered the same. The description and the drawings, which are not necessarily to scale, depict illustrative embodiments and are not intended to limit the scope of the disclosure.

A normal, healthy heart induces contraction by conducting intrinsically generated electrical signals throughout the heart. These intrinsic signals cause the muscle cells or tissue of the heart to contract. This contraction forces blood out of and into the heart, providing circulation of the blood throughout the rest of the body. However, many patients suffer from cardiac conditions that affect this contractility of their hearts. For example, some hearts may develop diseased tissues that no longer generate or conduct intrinsic electrical signals. In some examples, diseased cardiac tissues conduct electrical signals at differing rates, thereby causing an unsynchronized and inefficient contraction of the heart. In other examples, a heart may generate intrinsic signals at such a low rate that the heart rate becomes dangerously low. In still other examples, a heart may generate electrical signals at an unusually high rate. In some cases such an abnormality can develop into a fibrillation state, where the contraction of the patient's heart chambers are almost completely de-synchronized and the heart pumps very little to no blood. Implantable medical device which may be configured to determine occurrences of such cardiac abnormalities or arrhythmias and deliver one or more types of electrical stimulation therapy to patient's hearts may help to terminate or alleviate such cardiac conditions.

A variety of implantable devices may be used, either separately or in combination, to sense cardiac abnormalities or arrhythmias and to provide pacing or shocking, for example, if appropriate. It will be appreciated that strong magnetic fields, such as those present in and near an MRI machine, may create difficulties for implantable medical devices. In some embodiments, an implantable medical device such as those described herein may be configured to detect approach to a magnetic field, make appropriate alterations to its function, and notify other implantable medical devices about the magnetic field.

FIG. 1 is a schematic diagram showing a system 10 that includes a first implantable medical device 12 and a second implantable medical device 14. In some embodiments, first implantable medical device 12 may be configured to monitor a patient's heart rhythm and provide therapy if appropriate. In some embodiments, second implantable medical device 12 may be configured to monitor the patient's heart rhythm and provide therapy if appropriate. In some cases, first implantable medical device 12 is an SICD (subcutaneous implantable cardioverter) and second implantable medical device 14 is an LCP (leadless cardiac pacemaker), but this is not required in all cases.

As illustrated, system 10 is considered to be in the presence of an MRI machine 16. In some embodiments, first implantable medical device 12 may be configured to detect a magnetic field, such as that emanating from MRI machine 16. It will be appreciated that MRI machine 16, even when not operating, will emit a static magnetic field that is distinct from the additional magnetic fields that are emitted during operation. First implantable medical device 12 may be configured to communicate the presence of the magnetic field, indicative of the presence of MRI machine 16, to second implantable medical device 14. In some embodiments, this communication may include conducted communication through the body tissue of the patent, although other communication methods are contemplated including, for example, RF communication, optical communication, acoustic communication, or any other suitable communication. In some embodiments, conducted communication generally refers to an electrical signal that is transmitted, such as from one electrode to another electrode, through tissue. The tissue itself conducts the signal from one electrode to another.

Upon receiving an indication that a magnetic field indicative of an MRI machine (such as MRI machine 16) has been detected, second implantable medical device 14 may be programmed to enter an MRI-safe mode. In some cases, second implantable medical device 14 may remain in the MRI-safe mode until first implantable medical device 12 communicates cessation of the magnetic field indicative of an MRI machine. In some embodiments, second implantable medical device 14 may remain in the MRI-safe mode for a predetermined length of time that may be physician-programmable, based upon the therapeutic needs of the patient and/or their occupation. The details of what encompasses an MRI-safe mode may vary, depending on the specific function and programming of second implantable medical device 14.

In some embodiments, an MRI-safe mode includes modifying a therapy that would otherwise be provided by the second implantable medical device. In some cases, an MRI-safe mode includes ceasing the therapy that would otherwise be provided by the second implantable medical device and/or providing a sub-set or a different therapy protocol. In some instances, when the second implantable medical device 14 is a implantable cardiac pacemaker, the pacing therapy of the second implantable medical device may be changed from a synchronous pacing therapy to an asynchronous pacing therapy (AOO, VOO, DOO, etc.). Alternatively, or in addition, the energy level (e.g. amplitude and/or pulse width) of the pacing pulses may be increased in the MRI-safe mode to help the delivered pacing pulses capture the heart. Alternatively, or in addition, the pacing rate may be increased while in the MRI-safe mode to help the delivered pacing pulses capture the heart. These are just some example therapy changes than may be made in the MRI-safe mode.

The second implantable medical device 14 need not be a cardiac pacemaker. In some cases, the second implantable medical device 14 may be an implantable neuro-stimulation device, e.g. a vegal stimulation device, a deep brain stimulation device, a spinal cord stimulation device, a pain management neuro-stimulation device and/or any other suitable neuro-stimulation device. Such an implantable neuro-stimulation device may, for example, cease or change the delivered stimulation therapy when in an MRI-safe mode, and/or may stop or change sensing functions (if any) while in an MRI-safe mode. The normal operating mode, using the normal operational therapy, may be restored once the device is taken out of the MRI-safe mode.

In some embodiments, as illustrated, first implantable medical device 12 may include a beeper 18. In some embodiments, beeper 18 may be a piezoelectric beeper. Beeper 18 may be used by first implantable medical device 12, for example, to provide audible confirmation that a particular event has occurred, or that first implantable medical device 12 is functioning properly. Various tones or combinations of beeps may be used to provide a variety of different indications to the patient. In some embodiments, beeper 18 may be used by first implantable medical device 12 to provide the patient with an audible indication that a magnetic field indicative of an MRI machine has been detected. In some cases, first implantable medical device 12 may be further programmed to operate beeper 18 in order to provide the patient with an audible indication that the device has resumed normal operation once the magnetic field is no longer detected.

Detection of a magnetic field indicative of an MRI machine (such as MRI machine 16) may be accomplished in a variety of different ways. For example, a reed switch or a Hall-effect sensor, such as a tri-axial Hall-effect sensor, may be deployed within first implantable medical device 12. In some embodiments, such as sensor may instead be deployed in second implantable medical device 14, which can then inform first implantable medical device 12 (and any other devices) of the presence of a magnetic field indicative of an MRI. In some embodiments, a static magnetic field of about 0.2 Tesla may be sufficient to trigger detection.

In some embodiments, first implantable medical device 12 may include an inductive switching regulator type of power supply including a ferromagnetic core. Under strong magnetic fields, the core material can saturate. By including a core saturation detector, a high strength magnetic field such as that produced by an MRI machine 16 may be detected. Further details regarding magnetic field detection may be found in commonly owned U.S. Pat. No. 8,335,563, said patent is herein incorporated by reference in its entirety. It will be appreciated that other techniques for detecting magnetic fields may also be used, in addition to or instead of, the technology described therein.

Figure 2:
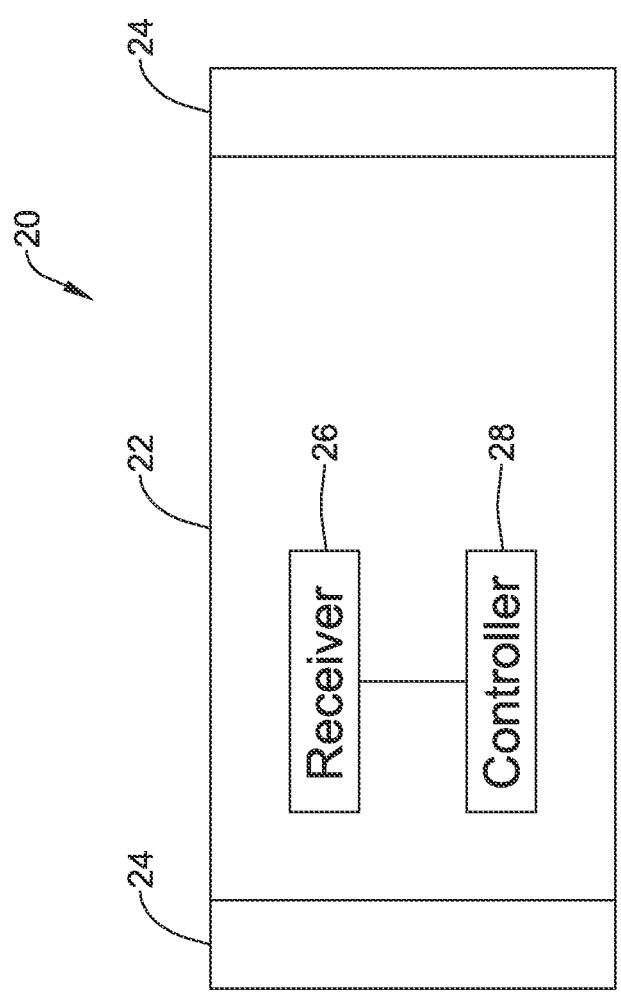
FIG. 2 is a schematic diagram illustrating a device useful in the system of FIG. 1.

FIG. 2 is a schematic diagram of an implantable medical device 20. In some embodiments, implantable medical device 20 is a Leadless Cardiac Pacemaker (LCP), but this is not required. The illustrative implantable medical device 20 includes a housing 22 and two or more electrodes 24 (two are illustrated) for receiving conducted communication signals emanating from outside of housing 22. A receiver 26 is coupled to electrodes 24 for receiving a communication via conducted communication, such as an electrical signal conducted through tissue, that indicates the presence of a magnetic field indicative from an MRI machine (such as MRI machine 16 of FIG. 1). In some embodiments, the electrodes 24 form part of an outer surface of implantable medical device 20. In the example shown, a controller 28 is coupled to receiver 26 and is configured to cause implantable medical device 20 to enter an MRI-safe mode upon receiving a communication that indicates the presence of the magnetic field indicative of an MRI machine. For example, in some embodiments, first implantable medical device 12 (FIG. 1) may provide the communication informing implantable medical device 20 of the presence of the magnetic field indicative of an MRI machine.

In some embodiments, controller 28 is configured to keep the implantable medical device 20 in the MRI-safe mode until a communication is received that indicates the cessation of the magnetic field indicative of an MRI machine. In some embodiments, controller 28 may be configured to remain in the MRI-safe mode for a predetermined amount of time. It will be appreciated that controller 28 may also be configured to regulate and/or control various operations of implantable medical device 20, including sensing and pacing functions.

In some embodiments, controller 28 is configured to, while in an operational mode, monitor a patient's heart rhythm and/or provide a patient therapy and, while in the MRI-safe mode, modify the monitoring of the patient's heart rhythm and/or modify the patient therapy relative to the operational mode. In some embodiments, controller 28 is configured, while in the MRI-safe mode, to cease the monitoring of the patient's heart rhythm and/or cease the patient therapy. In some embodiments, controller 28 is configured to, while in an operational mode, pace and/or sense a heart and, while in the MRI-safe mode, modify the pacing and/or sensing of the heart relative to the operational mode. In some embodiments, controller 28 is configured, while in the MRI-safe mode, to cease the pacing and/or sensing function. In some cases, controller 28 is configured, while in the MRI-safe mode, to modify the pacing and/or sensing function.

Figure 3:
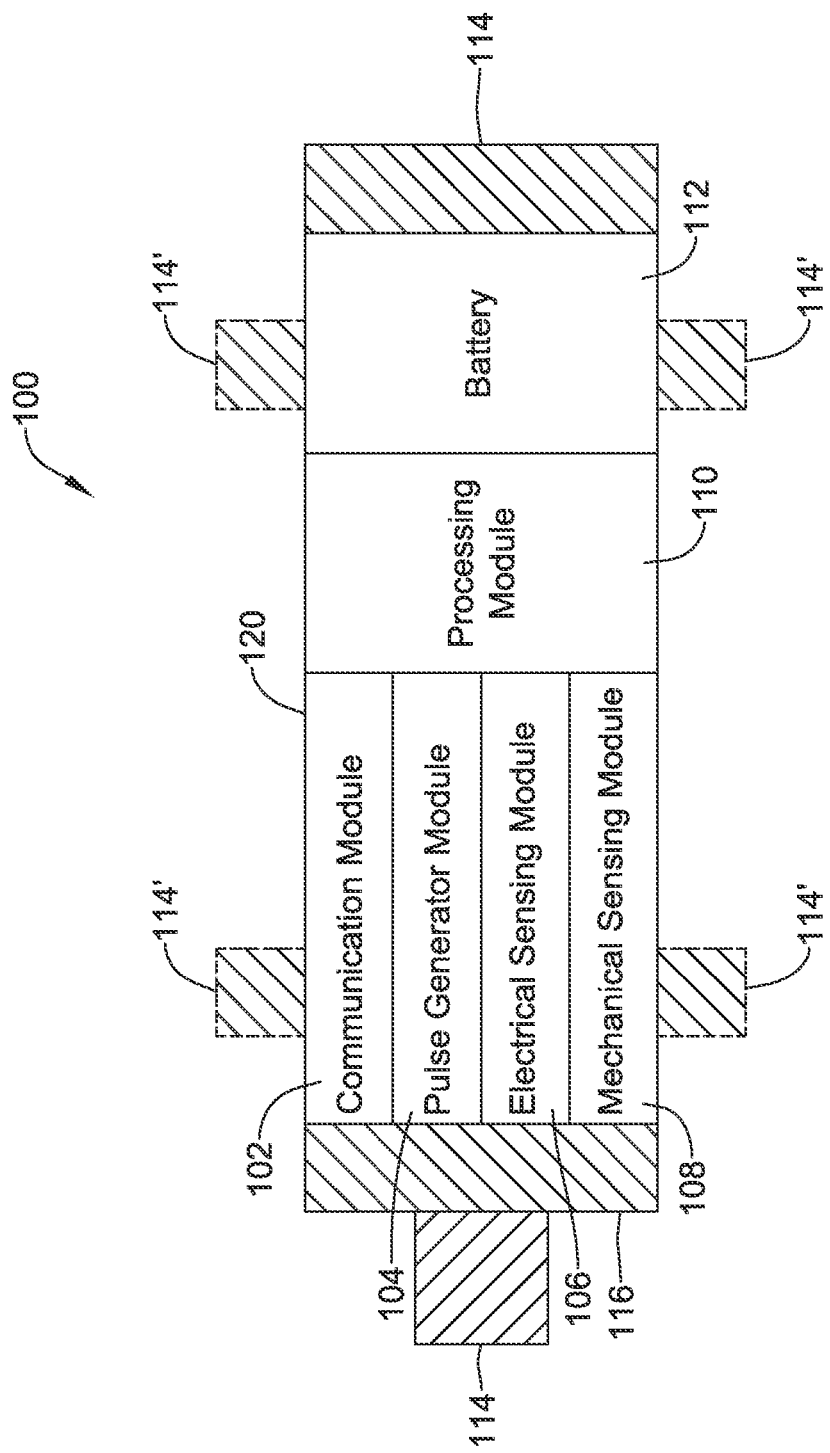
FIG. 3 is a schematic block diagram of an illustrative leadless cardiac pacemaker (LCP) according to one example of the present disclosure.

FIG. 3 depicts an exemplary leadless cardiac pacemaker (LCP) that may be implanted into a patient and may operate to prevent, control, or terminate cardiac events in patients, for example by appropriately employing one or more therapies such as anti-tachycardia pacing (ATP) therapy, cardiac resynchronization therapy (CRT), bradycardia therapy, defibrillation therapy, and/or the like. As can be seen in FIG. 3, LCP 100 may be a compact device with all components housed within LCP 100 or directly on housing 120. LCP 100 may be considered as being an example of implantable medical device 20 (FIG. 2). In the example shown in FIG. 3, LCP 100 may include a communication module 102, a pulse generator module 104, an electrical sensing module 106, a mechanical sensing module 108, a processing module 110, a battery 112, and electrodes 114. LCP 100 may include more or less modules, depending on the application.

Communication module 102 may be configured to communicate with devices such as sensors, other medical devices, and/or the like, that are located externally to LCP 100. Such devices may be located either external or internal to the patient's body. Irrespective of the location, external devices (i.e. external to the LCP 100 but not necessarily external to the patient's body) can communicate with LCP 100 via communication module 102 to accomplish one or more desired functions. For example, LCP 100 may communicate information, such as sensed electrical signals, data, instructions, messages, etc., to an external medical device through communication module 102. The external medical device may use the communicated signals, data, instructions and/or messages to perform various functions, such as determining occurrences of arrhythmias, delivering electrical stimulation therapy, storing received data, and/or performing any other suitable function. LCP 100 may additionally receive information such as signals, data, instructions and/or messages from the external medical device through communication module 102, and LCP 100 may use the received signals, data, instructions and/or messages to perform various functions, such as determining occurrences of arrhythmias, delivering electrical stimulation therapy, storing received data, and/or performing any other suitable function. Communication module 102 may be configured to use one or more methods for communicating with external devices. For example, communication module 102 may communicate via radiofrequency (RF) signals, inductive coupling, optical signals, acoustic signals, conducted communication signals, and/or any other signals suitable for communication.

In the example shown in FIG. 3, pulse generator module 104 may be electrically connected to electrodes 114. In some examples, LCP 100 may additionally include electrodes 114'. In such examples, pulse generator 104 may also be electrically connected to electrodes 114'. Pulse generator module 104 may be configured to generate electrical stimulation signals. For example, pulse generator module 104 may generate electrical stimulation signals by using energy stored in battery 112 within LCP 100 and deliver the generated electrical stimulation signals via electrodes 114 and/or 114'. Alternatively, or additionally, pulse generator 104 may include one or more capacitors, and pulse generator 104 may charge the one or more capacitors by drawing energy from battery 112. Pulse generator 104 may then use the energy of the one or more capacitors to deliver the generated electrical stimulation signals via electrodes 114 and/or 114'. In at least some examples, pulse generator 104 of LCP 100 may include switching circuitry to selectively connect one or more of electrodes 114 and/or 114' to pulse generator 104 in order to select which electrodes 114/114' (and/or other electrodes) pulse generator 104 delivers the electrical stimulation therapy. Pulse generator module 104 may generate electrical stimulation signals with particular features or in particular sequences in order to provide one or multiple of a number of different stimulation therapies. For example, pulse generator module 104 may be configured to generate electrical stimulation signals to provide electrical stimulation therapy to combat bradycardia, tachycardia, cardiac synchronization, bradycardia arrhythmias, tachycardia arrhythmias, fibrillation arrhythmias, cardiac synchronization arrhythmias and/or to produce any other suitable electrical stimulation therapy. Some more common electrical stimulation therapies include anti-tachycardia pacing (ATP) therapy, cardiac resynchronization therapy (CRT), and cardioversion/defibrillation therapy.

In some examples, LCP 100 may not include a pulse generator 104. For example, LCP 100 may be a diagnostic only device. In such examples, LCP 100 may not deliver electrical stimulation therapy to a patient. Rather, LCP 100 may collect data about cardiac electrical activity and/or physiological parameters of the patient and communicate such data and/or determinations to one or more other medical devices via communication module 102.

In some examples, LCP 100 may include an electrical sensing module 106, and in some cases, a mechanical sensing module 108. Electrical sensing module 106 may be configured to sense the cardiac electrical activity of the heart. For example, electrical sensing module 106 may be connected to electrodes 114/114', and electrical sensing module 106 may be configured to receive cardiac electrical signals conducted through electrodes 114/114'. The cardiac electrical signals may represent local information from the chamber in which LCP 100 is implanted. For instance, if LCP 100 is implanted within a ventricle of the heart, cardiac electrical signals sensed by LCP 100 through electrodes 114/114' may represent ventricular cardiac electrical signals. Mechanical sensing module 108 may include one or more sensors, such as an accelerometer, a blood pressure sensor, a heart sound sensor, a blood-oxygen sensor, a temperature sensor, a flow sensor and/or any other suitable sensors that are configured to measure one or more mechanical/chemical parameters of the patient. Both electrical sensing module 106 and mechanical sensing module 108 may be connected to a processing module 110, which may provide signals representative of the sensed mechanical parameters. Although described with respect to FIG. 3 as separate sensing modules, in some cases, electrical sensing module 206 and mechanical sensing module 208 may be combined into a single sensing module, as desired.

Electrodes 114/114' can be secured relative to housing 120 but exposed to the tissue and/or blood surrounding LCP 100. In some cases, electrodes 114 may be generally disposed on either end of LCP 100 and may be in electrical communication with one or more of modules 102, 104, 106, 108, and 110. Electrodes 114/114' may be supported by the housing 120, although in some examples, electrodes 114/114' may be connected to housing 120 through short connecting wires such that electrodes 114/114' are not directly secured relative to housing 120. In examples where LCP 100 includes one or more electrodes 114', electrodes 114' may in some cases be disposed on the sides of LCP 100, which may increase the number of electrodes by which LCP 100 may sense cardiac electrical activity, deliver electrical stimulation and/or communicate with an external medical device. Electrodes 114/114' can be made up of one or more biocompatible conductive materials such as various metals or alloys that are known to be safe for implantation within a human body. In some instances, electrodes 114/114' connected to LCP 100 may have an insulative portion that electrically isolates electrodes 114/114' from adjacent electrodes, housing 120, and/or other parts of the LCP 100.

Processing module 110 can be configured to control the operation of LCP 100. For example, processing module 110 may be configured to receive electrical signals from electrical sensing module 106 and/or mechanical sensing module 108. Based on the received signals, processing module 110 may determine, for example, occurrences and, in some cases, types of arrhythmias. Based on any determined arrhythmias, processing module 110 may control pulse generator module 104 to generate electrical stimulation in accordance with one or more therapies to treat the determined arrhythmia(s). Processing module 110 may further receive information from communication module 102. In some examples, processing module 110 may use such received information to help determine whether an arrhythmia is occurring, determine a type of arrhythmia, and/or to take particular action in response to the information. Processing module 110 may additionally control communication module 102 to send/receive information to/from other devices.

In some examples, processing module 110 may include a pre-programmed chip, such as a very-large-scale integration (VLSI) chip and/or an application specific integrated circuit (ASIC). In such embodiments, the chip may be pre-programmed with control logic in order to control the operation of LCP 100. By using a pre-programmed chip, processing module 110 may use less power than other programmable circuits (e.g. general purpose programmable microprocessors) while still being able to maintain basic functionality, thereby potentially increasing the battery life of LCP 100. In other examples, processing module 110 may include a programmable microprocessor. Such a programmable microprocessor may allow a user to modify the control logic of LCP 100 even after implantation, thereby allowing for greater flexibility of LCP 100 than when using a pre-programmed ASIC. In some examples, processing module 110 may further include a memory, and processing module 110 may store information on and read information from the memory. In other examples, LCP 100 may include a separate memory (not shown) that is in communication with processing module 110, such that processing module 110 may read and write information to and from the separate memory.

Battery 112 may provide power to the LCP 100 for its operations. In some examples, battery 112 may be a non-rechargeable lithium-based battery. In other examples, a non-rechargeable battery may be made from other suitable materials, as desired. Because LCP 100 is an implantable device, access to LCP 100 may be limited after implantation. Accordingly, it is desirable to have sufficient battery capacity to deliver therapy over a period of treatment such as days, weeks, months, years or even decades. In some instances, battery 112 may a rechargeable battery, which may help increase the useable lifespan of LCP 100. In still other examples, battery 112 may be some other type of power source, as desired.

To implant LCP 100 inside a patient's body, an operator (e.g., a physician, clinician, etc.), may fix LCP 100 to the cardiac tissue of the patient's heart. To facilitate fixation, LCP 100 may include one or more anchors 116. Anchor 116 may include any one of a number of fixation or anchoring mechanisms. For example, anchor 116 may include one or more pins, staples, threads, screws, helix, tines, and/or the like. In some examples, although not shown, anchor 116 may include threads on its external surface that may run along at least a partial length of anchor 116. The threads may provide friction between the cardiac tissue and the anchor to help fix the anchor 116 within the cardiac tissue. In other examples, anchor 116 may include other structures such as barbs, spikes, or the like to facilitate engagement with the surrounding cardiac tissue.

Figure 4:
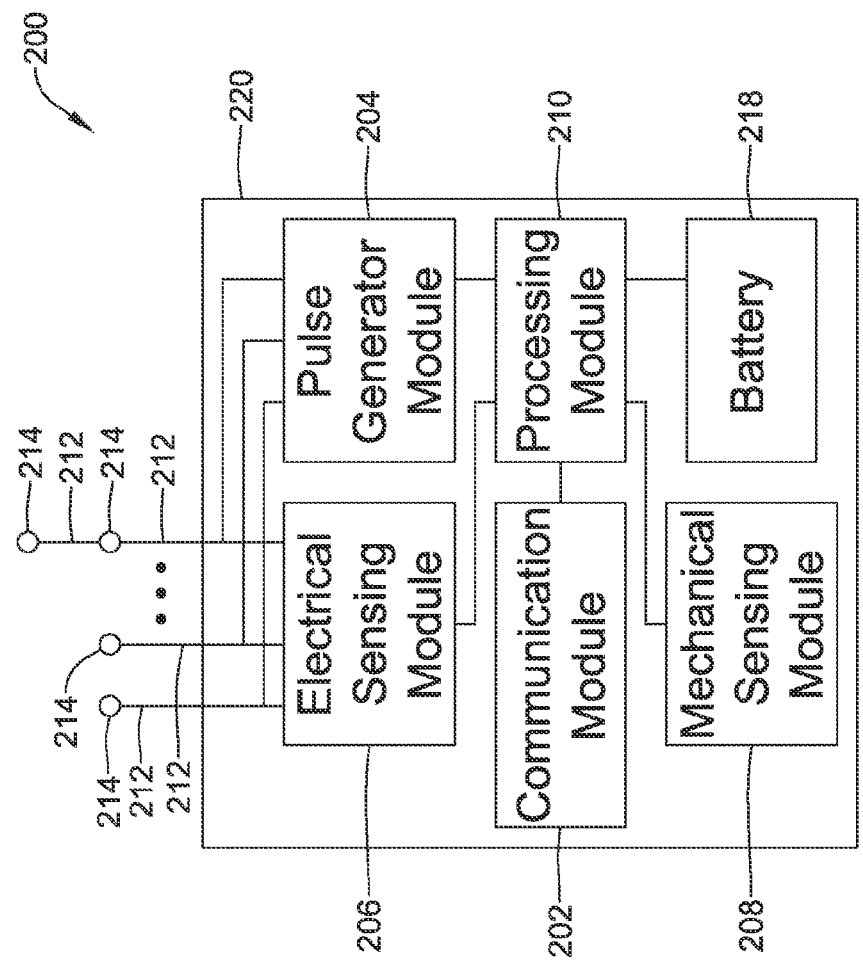
FIG. 4 is a schematic diagram of an implantable medical device according to an example of the present disclosure.

FIG. 4 depicts an example of another medical device (MD) 200, which may be used in conjunction with LCP 100 (FIG. 3) in order to detect and/or treat cardiac arrhythmias and other heart conditions. In the example shown, MD 200 may include a communication module 202, a pulse generator module 204, an electrical sensing module 206, a mechanical sensing module 208, a processing module 210, and a battery 218. Each of these modules may be similar to modules 102, 104, 106, 108, and 110 of LCP 100. Additionally, battery 218 may be similar to battery 112 of LCP 100. In some examples, however, MD 200 may have a larger volume within housing 220. In such examples, MD 200 may include a larger battery and/or a larger processing module 210 capable of handling more complex operations than processing module 110 of LCP 100.

While it is contemplated that MD 200 may be another leadless device such as shown in FIG. 3, in some instances MD 200 may include leads such as leads 212. Leads 212 may include electrical wires that conduct electrical signals between electrodes 214 and one or more modules located within housing 220. In some cases, leads 212 may be connected to and extend away from housing 220 of MD 200. In some examples, leads 212 are implanted on, within, or adjacent to a heart of a patient. Leads 212 may contain one or more electrodes 214 positioned at various locations on leads 212, and in some cases at various distances from housing 220. Some leads 212 may only include a single electrode 214, while other leads 212 may include multiple electrodes 214. Generally, electrodes 214 are positioned on leads 212 such that when leads 212 are implanted within the patient, one or more of the electrodes 214 are positioned to perform a desired function. In some cases, the one or more of the electrodes 214 may be in contact with the patient's cardiac tissue. In some cases, the one or more of the electrodes 214 may be positioned subcutaneously but adjacent the patient's heart. In some cases, electrodes 214 may conduct intrinsically generated electrical signals to leads 212, e.g. signals representative of intrinsic cardiac electrical activity. Leads 212 may, in turn, conduct the received electrical signals to one or more of the modules 202, 204, 206, and 208 of MD 200. In some cases, MD 200 may generate electrical stimulation signals, and leads 212 may conduct the generated electrical stimulation signals to electrodes 214. Electrodes 214 may then conduct the electrical signals and delivery the signals to the patient's heart (either directly or indirectly).

Mechanical sensing module 208, as with mechanical sensing module 108, may contain or be electrically connected to one or more sensors, such as accelerometers, blood pressure sensors, heart sound sensors, blood-oxygen sensors, and/or other sensors which are configured to measure one or more mechanical/chemical parameters of the heart and/or patient. In some examples, one or more of the sensors may be located on leads 212, but this is not required. In some examples, one or more of the sensors may be located in housing 220.

While not required, in some examples, MD 200 may be an implantable medical device. In such examples, housing 220 of MD 200 may be implanted in, for example, a transthoracic region of the patient. Housing 220 may generally include any of a number of known materials that are safe for implantation in a human body and may, when implanted, hermetically seal the various components of MD 200 from fluids and tissues of the patient's body.

In some cases, MD 200 may be an implantable cardiac pacemaker (ICP). In this example, MD 200 may have one or more leads, for example leads 212, which are implanted on or within the patient's heart. The one or more leads 212 may include one or more electrodes 214 that are in contact with cardiac tissue and/or blood of the patient's heart. MD 200 may be configured to sense intrinsically generated cardiac electrical signals and determine, for example, one or more cardiac arrhythmias based on analysis of the sensed signals. MD 200 may be configured to deliver CRT, ATP therapy, bradycardia therapy, and/or other therapy types via leads 212 implanted within the heart. In some examples, MD 200 may additionally be configured provide defibrillation therapy.

In some instances, MD 200 may be an implantable cardioverter-defibrillator (ICD). In such examples, MD 200 may include one or more leads implanted within a patient's heart. MD 200 may also be configured to sense cardiac electrical signals, determine occurrences of tachyarrhythmias based on the sensed signals, and may be configured to deliver defibrillation therapy in response to determining an occurrence of a tachyarrhythmia. In other examples, MD 200 may be a subcutaneous implantable cardioverter-defibrillator (S-ICD). In examples where MD 200 is an S-ICD, one of leads 212 may be a subcutaneously implanted lead. In at least some examples where MD 200 is an S-ICD, MD 200 may include only a single lead which is implanted subcutaneously, but this is not required.

In some examples, MD 200 may not be an implantable medical device. Rather, MD 200 may be a device external to the patient's body, and may include skin-electrodes that are placed on a patient's body. In such examples, MD 200 may be able to sense surface electrical signals (e.g. cardiac electrical signals that are generated by the heart or electrical signals generated by a device implanted within a patient's body and conducted through the body to the skin) In such examples, MD 200 may be configured to deliver various types of electrical stimulation therapy, including, for example, defibrillation therapy.

Figure 5:
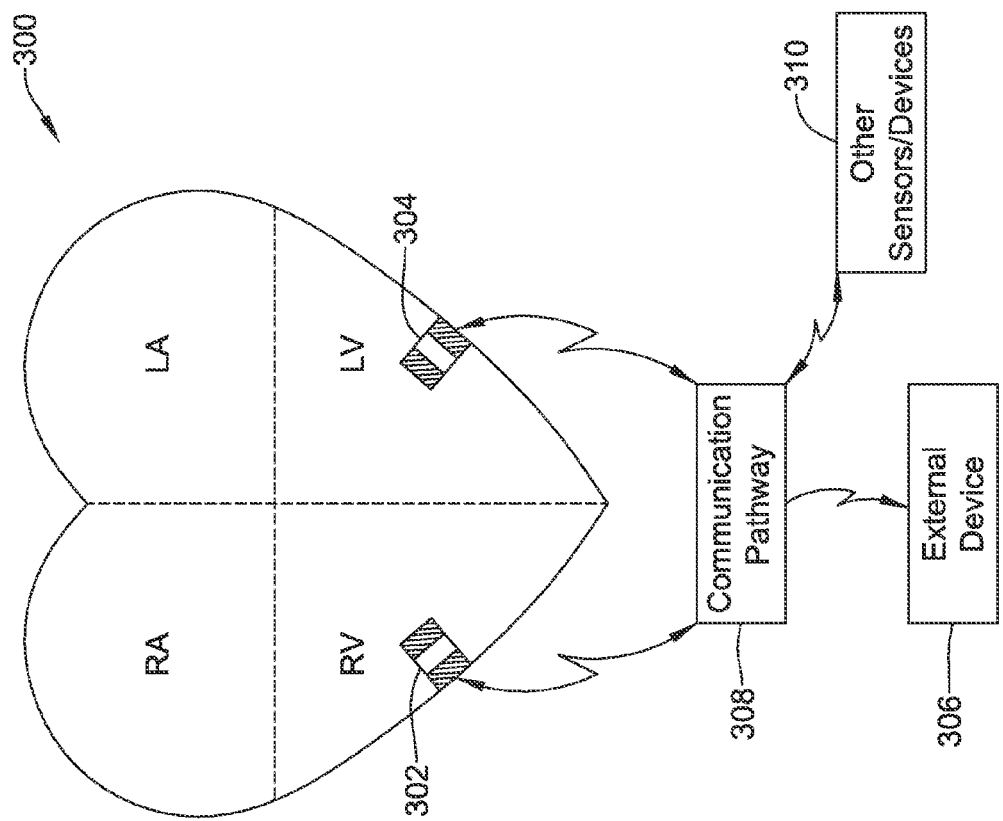
FIG. 5 is a schematic diagram of an exemplary medical system that includes multiple LCPs and/or other devices in communication with one another.

FIG. 5 illustrates an example of a medical device system and a communication pathway through which multiple medical devices 302, 304, 306, and/or 310 may communicate. In the example shown, medical device system 300 may include LCPs 302 and 304, external medical device 306, and other sensors/devices 310. External device 306 may be any of the devices described previously with respect to MD 200. Other sensors/devices 310 may also be any of the devices described previously with respect to MD 200. In some instances, other sensors/devices 310 may include a sensor, such as an accelerometer or blood pressure sensor, or the like. In some cases, other sensors/devices 310 may include an external programmer device that may be used to program one or more devices of system 300.

Various devices of system 300 may communicate via communication pathway 308. For example, LCPs 302 and/or 304 may sense intrinsic cardiac electrical signals and may communicate such signals to one or more other devices 302/304, 306, and 310 of system 300 via communication pathway 308. In one example, one or more of devices 302/304 may receive such signals and, based on the received signals, determine an occurrence of an arrhythmia. In some cases, device or devices 302/304 may communicate such determinations to one or more other devices 306 and 310 of system 300. In some cases, one or more of devices 302/304, 306, and 310 of system 300 may take action based on the communicated determination of an arrhythmia, such as by delivering a suitable electrical stimulation to the heart of the patient. It is contemplated that communication pathway 308 may communicate using RF signals, inductive coupling, optical signals, acoustic signals, or any other signals suitable for communication. Additionally, in at least some examples, device communication pathway 308 may comprise multiple signal types. For instance, other sensors/device 310 may communicate with external device 306 using a first signal type (e.g. RF communication) but communicate with LCPs 302/304 using a second signal type (e.g. conducted communication). Further, in some examples, communication between devices may be limited. For instance, as described above, in some examples, LCPs 302/304 may communicate with external device 306 only through other sensors/devices 310, where LCPs 302/304 send signals to other sensors/devices 310, and other sensors/devices 310 relay the received signals to external device 306.

In some cases, communication pathway 308 may include conducted communication. Accordingly, devices of system 300 may have components that allow for such conducted communication. For instance, the devices of system 300 may be configured to transmit conducted communication signals (e.g. current and/or voltage pulses) into the patient's body via one or more electrodes of a transmitting device, and may receive the conducted communication signals (e.g. pulses) via one or more electrodes of a receiving device. The patient's body may "conduct" the conducted communication signals (e.g. pulses) from the one or more electrodes of the transmitting device to the electrodes of the receiving device in the system 300. In such examples, the delivered conducted communication signals (e.g. pulses) may differ from pacing or other therapy signals. For example, the devices of system 300 may deliver electrical communication pulses at an amplitude/pulse width that is sub-threshold to the heart. Although, in some cases, the amplitude/pulse width of the delivered electrical communication pulses may be above the capture threshold of the heart, but may be delivered during a refractory period of the heart and/or may be incorporated in or modulated onto a pacing pulse, if desired.

Delivered electrical communication pulses may be modulated in any suitable manner to encode communicated information. In some cases, the communication pulses may be pulse width modulated or amplitude modulated. Alternatively, or in addition, the time between pulses may be modulated to encode desired information. In some cases, conducted communication pulses may be voltage pulses, current pulses, biphasic voltage pulses, biphasic current pulses, or any other suitable electrical pulse as desired.

Figure 6:
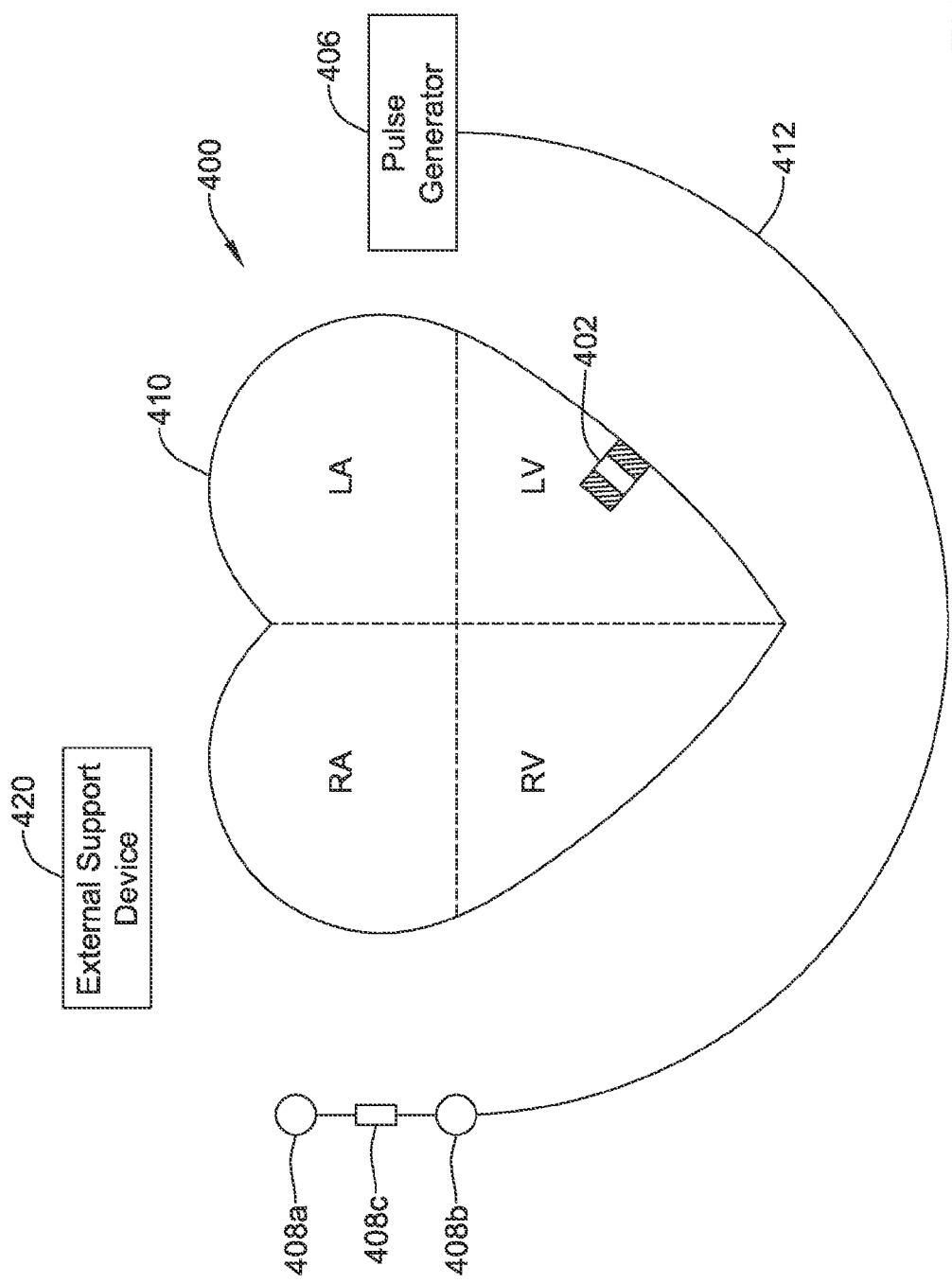
FIG. 6 is a schematic diagram of a system including an LCP and another medical device, in accordance with yet another example of the present disclosure.
Figure 7:
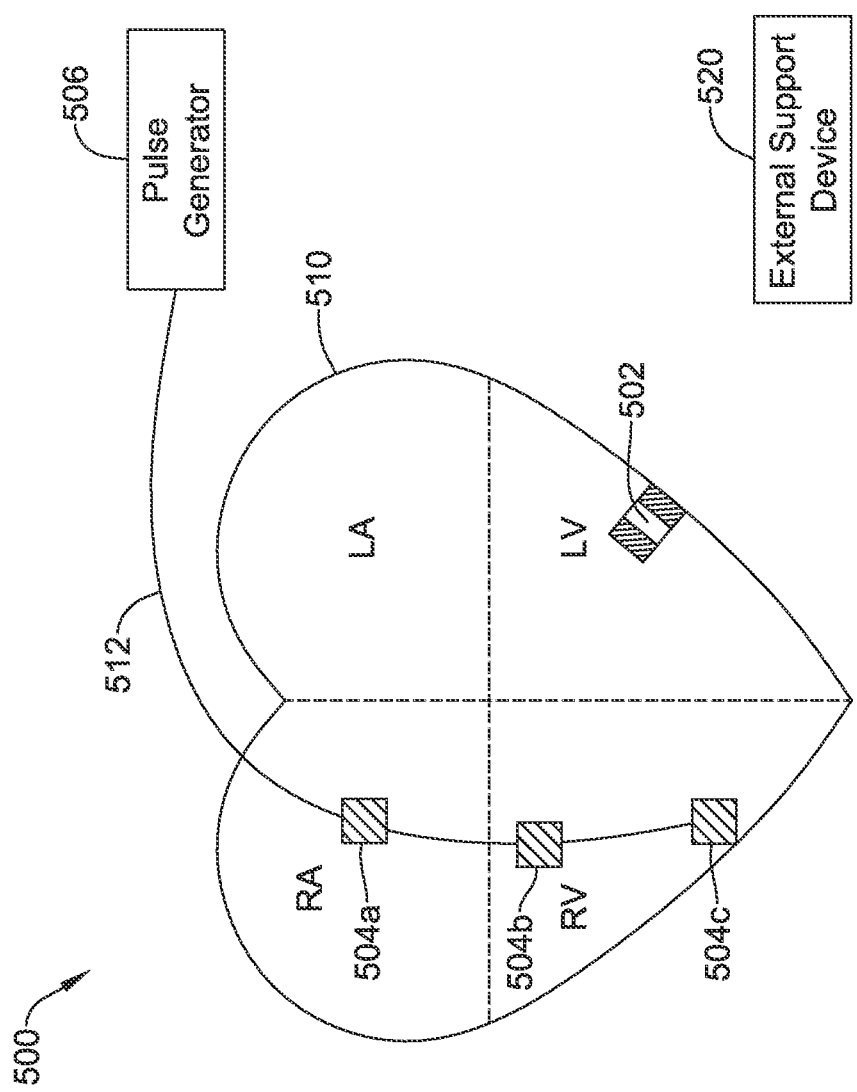
FIG. 7 is a schematic diagram of a system including an LCP and another medical device, in accordance with another example of the present disclosure.

FIGS. 6 and 7 show illustrative medical device systems that may be configured to operate according to techniques disclosed herein. In FIG. 6, an LCP 402 is shown fixed to the interior of the left ventricle of the heart 410, and a pulse generator 406 is shown coupled to a lead 412 having one or more electrodes 408a-408c. In some cases, the pulse generator 406 may be part of a subcutaneous implantable cardioverter-defibrillator (S-ICD), and the one or more electrodes 408a-408c may be positioned subcutaneously adjacent the heart. In some cases, the LCP 402 may communicate with the subcutaneous implantable cardioverter-defibrillator (S-ICD). In some cases, the LCP 302 may be in the right ventricle, right atrium or left atrium of the heart, as desired. In some cases, more than one LCP 302 may be implanted. For example, one LCP may be implanted in the right ventricle and another may be implanted in the right atrium. In another example, one LCP may be implanted in the right ventricle and another may be implanted in the left ventricle. In yet another example, one LCP may be implanted in each of the chambers of the heart.

In FIG. 7, an LCP 502 is shown fixed to the interior of the left ventricle of the heart 510, and a pulse generator 506 is shown coupled to a lead 512 having one or more electrodes 504a-504c. In some cases, the pulse generator 506 may be part of an implantable cardiac pacemaker (ICP) and/or an implantable cardioverter-defibrillator (ICD), and the one or more electrodes 504a-504c may be positioned in the heart 510. In some cases, the LCP 502 may communicate with the implantable cardiac pacemaker (ICP) and/or an implantable cardioverter-defibrillator (ICD).

The medical device systems 400 and 500 may also include an external support device, such as external support devices 420 and 520. External support devices 420 and 520 can be used to perform functions such as device identification, device programming and/or transfer of real-time and/or stored data between devices using one or more of the communication techniques described herein. As one example, communication between external support device 420 and the pulse generator 406 is performed via a wireless mode, and communication between the pulse generator 406 and LCP 402 is performed via a conducted mode. In some examples, communication between the LCP 402 and external support device 420 is accomplished by sending communication information through the pulse generator 406. However, in other examples, communication between the LCP 402 and external support device 420 may be via a communication module.

FIGS. 6-7 only illustrate two examples of medical device systems that may be configured to operate according to techniques disclosed herein. Other example medical device systems may include additional or different medical devices and/or configurations. For instance, other medical device systems that are suitable to operate according to techniques disclosed herein may include additional LCPs implanted within the heart. Another example medical device system may include a plurality of LCPs without other devices such as pulse generator 406 or 506, with at least one LCP capable of delivering defibrillation therapy. In yet other examples, the configuration or placement of the medical devices, leads, and/or electrodes may be different from those depicted in FIGS. 6 and 7. Accordingly, it should be recognized that numerous other medical device systems, different from those depicted in FIGS. 6 and 7, may be operated in accordance with techniques disclosed herein. As such, the examples shown in FIGS. 6 and 7 should not be viewed as limiting in any way.

Figure 8:
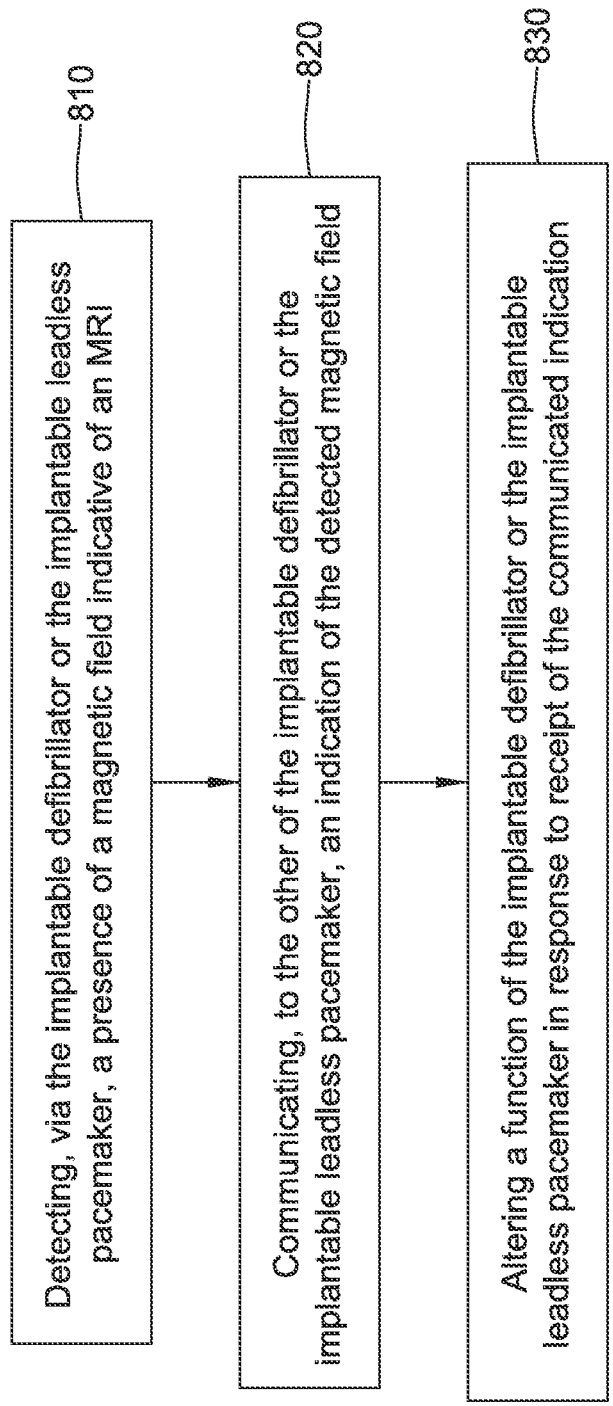
FIG. 8 is a flow diagram of an illustrative method that may be implemented by a medical device such as those illustrated in FIGS. 1-7.

FIG. 8 is a flow diagram illustrating a method that may be carried out using the implantable medical devices described herein. In some embodiments, FIG. 8 pertains to a cardiac rhythm management system including an implantable defibrillator and an implantable leadless pacemaker. As indicated at block 810, a presence of a magnetic field indicative of an MRI machine (such as MRI machine 16 of FIG. 1) is detected via an implantable defibrillator or an implantable leadless pacemaker. An indication of the detected magnetic field is communicated to the other of the implantable defibrillator or the implantable leadless pacemaker, as generally indicated at block 820. At block 830, a function of the implantable defibrillator or the implantable leadless pacemaker is altered in response to receipt of the communicated indication.

Figure 9:
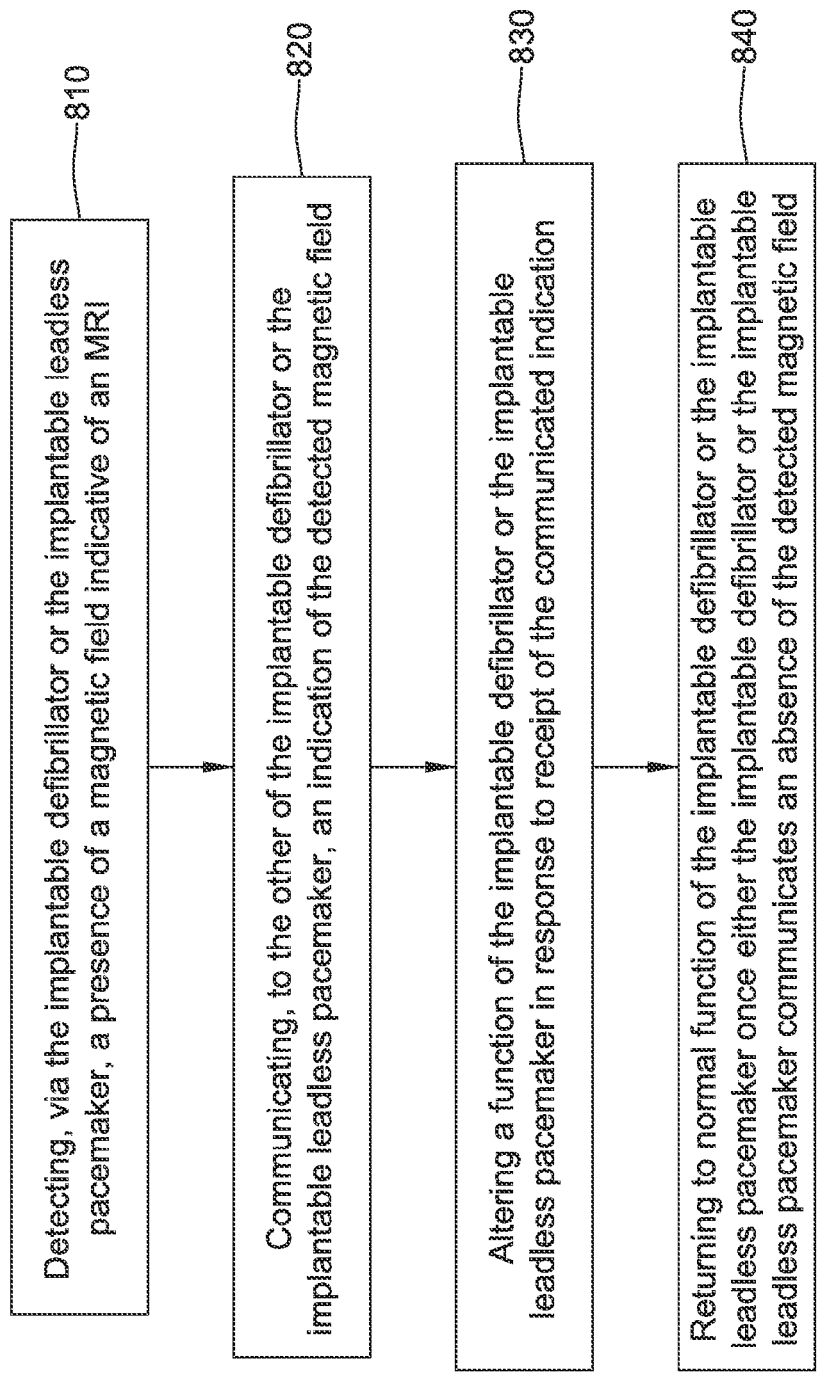
FIG. 9 is a flow diagram of an illustrative method that may be implemented by a medical device such as those illustrated in FIGS. 1-7.

FIG. 9 is a flow diagram illustrating a method that may be carried out with a cardiac rhythm management system including an implantable defibrillator and an implantable leadless pacemaker. As indicated at block 810, a presence of a magnetic field indicative of an MRI machine (such as MRI machine 16 of FIG. 1) is detected via an implantable defibrillator or an implantable leadless pacemaker. An indication of the detected magnetic field is communicated to the other of the implantable defibrillator or the implantable leadless pacemaker, as generally indicated at block 820. At block 830, a function of the implantable defibrillator or the implantable leadless pacemaker is altered in response to receipt of the communicated indication. In some embodiments, and as indicated at block 840, the implantable defibrillator or the implantable leadless pacemaker may return to normal function once either the implantable defibrillator or the implantable leadless pacemaker communicates an absence of the detected magnetic field.

Figure 10:
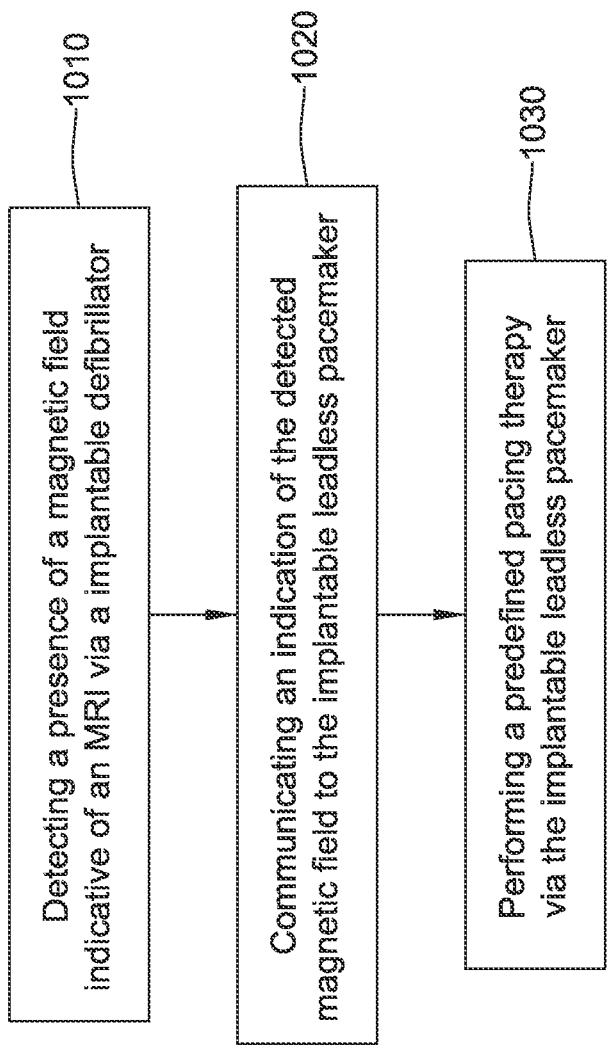
FIG. 10 is a flow diagram of an illustrative method that may be implemented by a medical device such as those illustrated in FIGS. 1-7.

FIG. 10 is a flow diagram illustrating a method that may be carried out with a cardiac rhythm management system including an implantable defibrillator and an implantable leadless pacemaker. As indicated at block 1010, a presence of a magnetic field indicative of an MRI machine (such as MRI machine 16 of FIG. 1) is detected via an implantable defibrillator. An indication of the detected magnetic field is communicated to the implantable leadless pacemaker, as generally indicated at block 1020. At block 1030, the implantable leadless pacemaker performs a predefined pacing therapy. The predefined pacing therapy may, for example, include pacing at a predetermined heart rate, pacing in accordance with a predetermined asynchronous pacing protocol (AOO, VOO, DOO, etc.), pacing with pacing pulses with a predetermined energy level (e.g. amplitude and/or pulse width), etc. These are just some examples.

Those skilled in the art will recognize that the present disclosure may be manifested in a variety of forms other than the specific examples described and contemplated herein. For instance, as described herein, various examples include one or more modules described as performing various functions. However, other examples may include additional modules that split the described functions up over more modules than that described herein. Additionally, other examples may consolidate the described functions into fewer modules. Accordingly, departure in form and detail may be made without departing from the scope and spirit of the present disclosure as described in the appended claims.

What is claimed is:

1. A cardiac rhythm management system comprising:
   a first implantable medical device configured to monitor a patient's heart rhythm and provide therapy if appropriate, the first implantable medical device is further configured to detect a magnetic field indicative of an MRI;
   a second implantable medical device configured to monitor a patient's heart rhythm and provide therapy if appropriate; and
   wherein the first implantable medical device, upon detecting a magnetic field indicative of an MRI, is further configured to communicate the presence of the magnetic field indicative of the MRI to the second implantable medical device.

2. The cardiac rhythm management system of claim 1, wherein the first implantable medical device is configured to communicate the presence of the magnetic field indicative of an MRI via conducted communication.

3. The cardiac rhythm management system of claim 1, wherein the second implantable medical device, upon being informed of the presence of the magnetic field indicative of an MRI, is programmed to enter an MRI-safe mode until the first implantable medical device communicates cessation of the magnetic field indicative of an MRI.

4. The cardiac rhythm management system of claim 3, wherein an MRI-safe mode comprises modifying the therapy that would otherwise be provided by the second implantable medical device.

5. The cardiac rhythm management system of claim 3, wherein an MRI-safe mode comprises ceasing the therapy that would otherwise be provided by the second implantable medical device.

6. The cardiac rhythm management system of claim 1, wherein the first implantable medical device is configured to communicate the presence of a magnetic field indicative of an MRI upon detecting a static magnetic field having a strength of at least about 0.2 Tesla.

7. The cardiac rhythm management system of claim 1, wherein the first implantable medical device includes a beeper and is programmed to operate the beeper to provide the patient with an audible indication that a magnetic field indicative of an MRI has been detected.

8. The cardiac rhythm management system of claim 7, wherein the first implantable medical device is further programmed to operate the beeper to provide the patient with an audible indication that the device has resumed normal operation once the magnetic field is no longer detected.

9. The cardiac rhythm management system of claim 1, wherein the first implantable medical device is an SICD and the second implantable medical device is a leadless cardiac pacemaker.

10. The cardiac rhythm management system of claim 1, wherein the first implantable medical device is an ICD and the second implantable medical device is one of a neurostimulator, a deep brain stimulator and a spinal cord stimulator.

11. A leadless cardiac pacemaker (LCP), comprising:
    a housing;
    two or more electrodes for receiving conducted communication signals emanating from outside of the housing;
    a receiver coupled to the two or more electrodes for receiving a communication via conducted communication that indicates the presence of a magnetic field indicative from an MRI; and
    a controller coupled to the receiver, the controller configured to cause the leadless cardiac pacemaker to enter an MRI-safe mode upon receiving the communication that indicates the presence of the magnetic field indicative of an MRI.

12. The leadless cardiac pacemaker (LCP) of claim 11, wherein the controller is configured to remain in the MRI-safe mode until a communication is received that indicates the cessation of the magnetic field indicative of an MRI.

13. The leadless cardiac pacemaker (LCP) of claim 11, wherein:
    in an operational mode, the controller is configured to monitor a patient's heart rhythm and/or provide a patient therapy; and
    in the MRI-safe mode, the controller is configured to modify the monitoring of the patient's heart rhythm and/or modify the patient therapy relative to the operational mode.

14. The leadless cardiac pacemaker (LCP) of claim 11, wherein:
    in an operational mode, the controller is configured to monitor a patient's heart rhythm and/or provide a patient therapy; and
    in the MRI-safe mode, the controller is configured to cease the monitoring of the patient's heart rhythm and/or cease the patient therapy.

15. The leadless cardiac pacemaker (LCP) of claim 11, wherein:
    in an operational mode, the controller is configured to pace and/or sense a heart; and
    in the MRI-safe mode, the controller is configured to modify the pacing and/or sensing of the heart relative to the operational mode.

16. The leadless cardiac pacemaker (LCP) of claim 11, wherein:
    in an operational mode, the controller is configured to pace and/or sense a heart; and
    in the MRI-safe mode, the controller is configured to cease the pacing and/or sensing.

17. The leadless cardiac pacemaker (LCP) of claim 11, wherein the two or more electrodes form part of an outer surface of the leadless cardiac pacemaker (LCP).

18. A method of operating a cardiac rhythm management system including an implantable defibrillator and an implantable leadless pacemaker, the method comprising:
    detecting, via the implantable defibrillator or the implantable leadless pacemaker, a presence of a magnetic field indicative of an MRI;
    communicating, to the other of the implantable defibrillator or the implantable leadless pacemaker, an indication of the detected magnetic field; and
    altering a function of the implantable defibrillator or the implantable leadless pacemaker in response to receipt of the communicated indication.

19. The method of claim 18, further comprising returning to normal function of the implantable defibrillator or the implantable leadless pacemaker once either the implantable defibrillator or the implantable leadless pacemaker communicates an absence of the detected magnetic field.

20. The method of claim 18, wherein the implantable defibrillator detects the magnetic field and communicates the indication of the detected magnetic field to the implantable leadless pacemaker, and in response the implantable leadless pacemaker performs a predefined pacing therapy.

* * * * *